(12) United States Patent
Torisu et al.

(10) Patent No.: US 6,955,801 B2
(45) Date of Patent: Oct. 18, 2005

(54) HIGH-PURITY FLUORINE GAS, PRODUCTION AND USE THEREOF, AND METHOD FOR ANALYZING TRACE IMPURITIES IN HIGH-PURITY FLUORINE GAS

(75) Inventors: Junichi Torisu, Kawasaki (JP); Hitoshi Atobe, Kawasaki (JP); Yasuyuki Hoshino, Kawasaki (JP)

(73) Assignee: Showa Denka K.K., Tokyo (JP)

( * ) Notice: Subject to any disclaimer, the term of this patent is extended or adjusted under 35 U.S.C. 154(b) by 0 days.

(21) Appl. No.: 10/362,876

(22) PCT Filed: Jun. 27, 2002

(86) PCT No.: PCT/JP02/06519

§ 371 (c)(1),
(2), (4) Date: Feb. 27, 2003

(87) PCT Pub. No.: WO03/002454

PCT Pub. Date: Jan. 9, 2003

(65) Prior Publication Data

US 2004/0028600 A1 Feb. 12, 2004

Related U.S. Application Data

(60) Provisional application No. 60/306,421, filed on Jul. 20, 2001, and provisional application No. 60/306,422, filed on Jul. 20, 2001.

(30) Foreign Application Priority Data

Jun. 29, 2001 (JP) .......................... 2001-199437
Jun. 29, 2001 (JP) .......................... 2001-199731

(51) Int. Cl.$^7$ .......................... C01B 7/20; G01N 30/14; G01N 30/88
(52) U.S. Cl. .......................... 423/500; 423/503; 423/504; 436/124
(58) Field of Search .......................... 423/500, 464, 423/503, 504; 436/124

(56) References Cited

U.S. PATENT DOCUMENTS

| | | | |
|---|---|---|---|
| 3,989,808 A | | 11/1976 | Asprey |
| 4,292,287 A | | 9/1981 | Orlett et al. |
| 4,711,680 A | * | 12/1987 | Christe .................. 149/109.4 |
| 5,017,499 A | * | 5/1991 | Hakuta et al. ............ 436/124 |
| 5,363,396 A | | 11/1994 | Webb et al. |
| 5,396,514 A | * | 3/1995 | Voss .......................... 372/57 |
| 6,280,597 B1 | * | 8/2001 | Kashiwada et al. ........ 205/172 |
| 6,609,540 B1 | * | 8/2003 | Torisu et al. ............ 137/896 |

FOREIGN PATENT DOCUMENTS

| | | |
|---|---|---|
| DE | 196 18 119 | 11/1996 |
| DE | 196 18 119 A1 | 11/1996 |
| EP | 0 902 101 A1 | 3/1999 |
| EP | 0 957 351 A2 | 11/1999 |
| GB | 2 240 639 A | 8/1991 |
| JP | 7-287001 | 10/1995 |
| JP | 2001-7423 | 1/2001 |

OTHER PUBLICATIONS

Derwent Abstract Accession No. 1996–007350, "Analysing impurity gases in fluorine gas by passing sample fluorine gas contg. impurity gases through metal fluoride layer . . . and then analysing by gas chromatography" (corresponding to JP 07287001–Oct. 31, 1995).*

EPO Form 210 with attachment, for PCT/JP02/06519, date–stamped Feb. 24, 2004, as accessed at www.eponline.org on Jun. 5, 2004.*

Patent Abstracts of Japan vol. 2000, No. 16, May 8, 2001 & JP 2001 007423 A (Showa Denko KK), Jan. 12, 2001 abstract.

Patent Abstracts of Japan vol. 1996, No. 02, Feb. 29, 1996 & JP 07 287001 A (Kanto Denka Kogyo Co Ltd), Oct. 31, 1995 abstract.

* cited by examiner

Primary Examiner—Stanley S. Silverman
Assistant Examiner—Ardith E Hertzog
(74) Attorney, Agent, or Firm—Sughrue Mion, PLLC

(57) ABSTRACT

A step (1) of heating a fluoronickel compound to release a fluorine gas, a step (2) of allowing a fluorine gas to be occluded into a fluorinated compound, and a step (3) of heating the fluoronickel compound and reducing an inner pressure are conducted in a container, respectively, at least once, and thereafter a high-purity fluorine gas is obtained in the step (1). Also, a step (5) of heating a fluoronickel compound and reducing an inner pressure and a step (6) of allowing a fluorine gas reduced in a hydrogen fluoride content to be occluded into the fluoronickel compound are conducted in a container having a fluorinated layer formed on its surface, respectively, at least once, the step (5) is further conducted, and thereafter a fluorine gas containing impurity gases is contacted with the fluoronickel compound to fix and remove the fluorine gas, and the impurities are analyzed by gas chromatography.

9 Claims, 3 Drawing Sheets

HIGH-PURITY FLUORINE GAS, PRODUCTION AND USE THEREOF, AND METHOD FOR ANALYZING TRACE IMPURITIES IN HIGH-PURITY FLUORINE GAS

CROSS-REFERENCE TO RELATED APPLICATIONS

This application claims benefit pursuant to 35 U.S.C. §119(e)(1) of the filing date of the Provisional Application 60/306,421 filed Jul. 20, 2001, and the filing date of the Provisional Application 60/306,422 filed Jul. 20, 2001.

This application is an application filed under 35 U.S.C. §111(a) claiming benefit pursuant to 35 U.S.C. §119(e)(1) of the filing date of the Provisional Application 60/306,421 filed Jul. 20, 2001, and the filing date of the Provisional Application 60/306,422 filed Jul. 20, 2001, pursuant to 35 U.S.C. §111(b).

TECHNICAL FIELD

The present invention relates to a high-purity fluorine gas, the production and use thereof, and a method for analyzing trace impurities in a high-purity fluorine gas. Particularly, the present invention relates to a process for producing a high-purity fluorine gas, a high-purity fluorine gas and a high-purity fluoronickel compound obtained thereby, and the use of the high-purity fluorine gas, and further relates to a method for analyzing trace impurities in a high-purity fluorine gas.

BACKGROUND ART

A fluorine gas is a combustion-supporting gas having strong oxidative property and also has strong toxicity and corrosiveness and therefore, in Japan, fluorine gas is scarcely traded on a commercial base except in a special case. Japanese International Application Domestic Publication No. 5-502981 describes a halogen generator, where fluorine (a halogen) is stored in the form of being occluded into a solid and on use of fluorine, the container housing the solid is heated to generate fluorine (a halogen). In this publication, it is stated that when $K_3NiF_7$ is used as a substance for occluding fluorine, fluorine having a purity of 99.7% can be continuously supplied. In general uses, a fluorine gas having a purity on the order of 99.7% can be used, however, in the field of production of semiconductors, for example, a fluorine gas having a high purity of 99.7% or more is demanded.

On the other hand, the fluorine gas being supplied on a commercial basis generally contains about 1.5 vol % of impurities. The majority of the impurities are $N_2$, $O_2$, $CO_2$, fluorocarbons such as $CF_4$, and gases such as $SF_6$, $SiF_4$ and HF. In the case of using a fluorine gas containing these impurities for the purpose of synthesizing a fluorine compound, these impurities have almost no effect and a purity of 98 to 99 vol % is sufficient. With respect to the method for analyzing a fluorine gas having a purity of 98 to 99 vol %, a volumetric titration method of allowing a fluorine gas to be absorbed in an aqueous KI solution and measuring liberated $I_2$ using a $Na_2S_2O_3$ solution, and an Orsat method of allowing a fluorine gas to react with and be absorbed in a KI solution and analyzing the purity from the volume of undissolved gas are known. In the Orsat method, when undissolved gas collected is analyzed by gas chromatography utilizing the low solubility of impurities such as $N_2$, $O_2$, $CO_2$, fluorocarbon (e.g., $CF_4$) and $SF_6$ in a KI solution, the composition of the impurities can also be analyzed.

However, these analysis methods cannot be an optimal method as the analysis method for a high-purity fluorine gas, containing trace impurities in a concentration of hundreds of vol. ppm or less, even though such high-purity fluorine gas is an important key technology for the development of semiconductor industry. Fluorine gas is difficult to handle because it is highly reactive (oxidative) and in turn highly corrosive. Therefore, fluorine gas cannot be introduced directly into an analyzer. Even in the case of gas chromatography which is effective for analyzing the composition of gas components, almost no method has been heretofore known for the analysis of trace impurities in a fluorine gas, because, for example, there is no appropriate separation column where fluorine gas can be directly introduced.

Fluorine gas is used as an etching gas or a cleaning gas in the semiconductor industry because of its reaction properties. Particularly, in uses for annealing metal fluoride for optical materials or as a gas for an excimer laser, the optical properties of fluorine are also important and the amount of fluorine gas used for this purpose is increasing. Accompanying these demands, a high-purity fluorine gas and an analysis method therefor are strongly required. For optical uses, a high-purity fluorine gas reduced in impurities such as $N_2$, $O_2$, $CO_2$, fluorocarbon (e.g., $CF_4$), $SF_6$, $SiF_4$ and HF, and having a purity of 99.9 to 99.99 vol % is demanded. In particular, a high-purity fluorine gas having an $O_2$ gas concentration of several vol ppm or less and a purity of 99.99 vol % or more is demanded.

Japanese Unexamined Patent Publication No. 4-9757 (JP-A-4-9757) describes a technique where a fluorine gas containing impurities is passed through a metal chloride-filled layer to convert the fluorine gas into a chlorine gas, the chlorine gas is fixed and removed by reacting the chlorine gas with an alkali metal aqueous solution and a metal or separated and removed by the adsorption to a porous polymer, and the separated impurities are analyzed by a gas chromatography. Also, Japanese Unexamined Patent Publication No. 7-287001 (JP-A-7-287001) describes a technique of heating cobalt difluoride ($CoF_2$) at 200 to 300° C. to fix a fluorine gas as cobalt trifluoride ($CoF_3$) and analyzing trace impurities separated from the fluorine gas using a gas chromatography.

In the reaction with a fluorine gas, both the metal chloride (NaCl) and cobalt difluoride ($CoF_2$) show a low reaction rate at room temperature and to attain a complete reaction, a temperature of 100 to 300° C. is necessary. However, in these methods, for example, at the time of fixing a fluorine gas as a metal fluoride by the displacement with chlorine of a metal chloride, $O_2$, which is one component of impurities in the fluorine gas, is generated. It is also found that if the sampling and sample measuring tubes, containers for filling metal chloride, flow path changeover valve and the like are not subjected to an inner surface treatment, generation of $O_2$ and HF occurs, which is considered to be ascribable to the water adsorbed to the metal inner surface. This phenomenon cannot be overcome merely by a baking treatment and, due to the increase of $O_2$ background, these methods cannot be accurate as a quantitative analysis method of trace oxygen gas in a fluorine gas.

The method described in JP-A-4-9757 is a method where the chlorine gas generated by the conversion of a fluorine gas is absorbed and reacted in an aqueous solution of alkali metal hydroxide and thereby removed and separated and thereafter, the impurities are analyzed by gas chromatography. In the case of analyzing trace impurities, the dissolution and absorption of impurities in the aqueous solution raise a problem and in some cases, the quantitative analysis cannot be exactly performed. If the purpose is to analyze the impurities in a chlorine gas, the gas chromatography method described in this patent publication may be a general and good method, where a chlorine gas is separated from impurities, using a separation column packed with porous polymer beads, by a pre-cut or backflash system and if desired, a separation column such as MS-5A is employed. However, the problem of impurities, particularly oxygen, generated in the previous stage from the inner surface of equipment or material coming into contact with the fluorine gas or from the fluorine gas-removing and separating agent still remains unsolved.

If this problem can be solved, $H_2$, $O_2$, $N_2$, $CH_4$, CO, $CO_2$, fluorocarbon (e.g., $CF_4$) and $SF_6$ out of impurities in a fluorine gas may be analyzed by the analysis method described in those patent publications. However, other than these impurities, the fluorine gas contains impurities such as HF, $SiF_4$ and other metal fluorides and unless these impurities can be analyzed, the method cannot be said to attain a function as an analysis method of trace impurities.

DISCLOSURE OF INVENTION

The present invention has been made under these circumstances and an object of the present invention is to provide a process for producing high-purity fluorine gas usable, for example, as an excimer laser gas, a high-purity fluorine gas, and a high-purity fluoronickel compound obtained thereby, and the use of a high-purity fluorine gas obtained thereby.

A further object of the present invention is to provide a method for analyzing trace impurities in a high-purity fluorine gas, where the contamination from a metal material coming into contact with a fluorine gas or from fluorine gas-removing and separating agent is prevented.

As a result of extensive investigations to solve the above-described problems, the present inventors have found that the above-described objects can be attained by using a process for producing a high-purity fluorine gas, comprising conducting a step (1) of heating a fluoronickel compound filled in a container to release a fluorine gas and a step (2) of allowing a fluorine gas to be occluded into a fluoronickel compound filled in a container, and thereafter obtaining a high-purity fluorine gas in the step (1), which comprises conducting the steps (1) and (2) as well as a step (3) of heating the fluoronickel compound filled in a container at 250 to 600° C. and reducing a pressure inside the container to 0.01 MPa (absolute pressure) or less, respectively, at least once and thereafter, a high-purity fluorine gas is obtained in the step (1).

The present invention also provides a high-purity fluorine gas recovered, after a step (1) of heating a fluoronickel compound filled in a container to release a fluorine gas and a step (2) of allowing a fluorine gas to be occluded into a fluoronickel compound filled in a container are conducted, in the step (1), which is recovered in the step (1), after the step (2) in which a fluorine gas reduced in a hydrogen fluoride content to 500 vol ppm or less is occluded as well as a step (3) of heating the fluoronickel compound filled in a container at 250 to 600° C. and reducing a pressure inside the container to 0.01 MPa (absolute pressure) or less are conducted, respectively, at least once.

The present invention further provides a high-purity fluorine gas recovered, after a step (1) of heating a fluoronickel compound filled in a container to release a fluorine gas and a step (2) of allowing a fluorine gas to be occluded into a fluoronickel compound filled in a container are conducted, in the step (1), which is recovered in the step (1), after the step (2) in which a fluorine gas reduced in a hydrogen fluoride content to 500 vol ppm or less is occluded as well as a step (3) of heating the fluoronickel compound filled in a container at 250 to 600° C. and reducing a pressure inside the container to 0.01 MPa (absolute pressure) or less and a step (4) of reducing a pressure inside the container filled with the fluoronickel compound to 0.01 MPa (absolute pressure) or less at a temperature of less than 250° C., are conducted, respectively, at least once.

The present invention further provides an excimer laser gas comprising the high-purity fluorine gas described above.

The present invention further provides an high-purity fluoronickel compound capable of repeatedly conducting occlusion and release of a fluorine gas and releasing a high-purity fluorine gas, which is obtained by conducting a step (4) of reducing the pressure inside a container filled with a fluoronickel compound to 0.01 MPa (absolute pressure) or less at a temperature of less than 250° C., a step (3) of heating the fluoronickel compound filled in the container at 250 to 600° C. and reducing the pressure inside the container to 0.01 MPa (absolute pressure) or less, and a step of occluding a fluorine gas reduced in the hydrogen fluoride content to 500 vol ppm or less, respectively, at least once.

The present inventors have also found that the above-described problems can be solved by using a method for analyzing trace impurities in a high-purity fluorine gas, comprising filling a fluoronickel compound in a container comprising a metal material or a metal material having a nickel film, the container having a fluorinated layer formed on a surface of the metal material or nickel film, conducting a step (5) of heating the fluoronickel compound to 250 to 600° C. and reducing a pressure inside the container to 0.01 MPa (absolute pressure) or less, and a step (6) of allowing a fluorine gas reduced in a hydrogen fluoride content to 500 vol ppm or less to be occluded into the fluoronickel compound passed through the step (5), respectively, at least once, and further conducting the step (5), then contacting a fluorine gas containing impurity gases with the fluoronickel compound at 200 to 350° C. to fix and remove the fluorine gas, and analyzing the impurities by gas chromatography. The present invention has been accomplished based on this finding.

The present invention further provides a method for analyzing trace impurities in a high-purity fluorine gas, comprising introducing a fluorine gas containing impurity gases into a cell with a material of window being composed of a metal halide, and analyzing the impurities by infrared spectrometry, the method using an apparatus where a fluorinated layer is formed on a surface of a metal material or metal material having nickel film which comes into contact with the fluorine gas.

Figure 1:
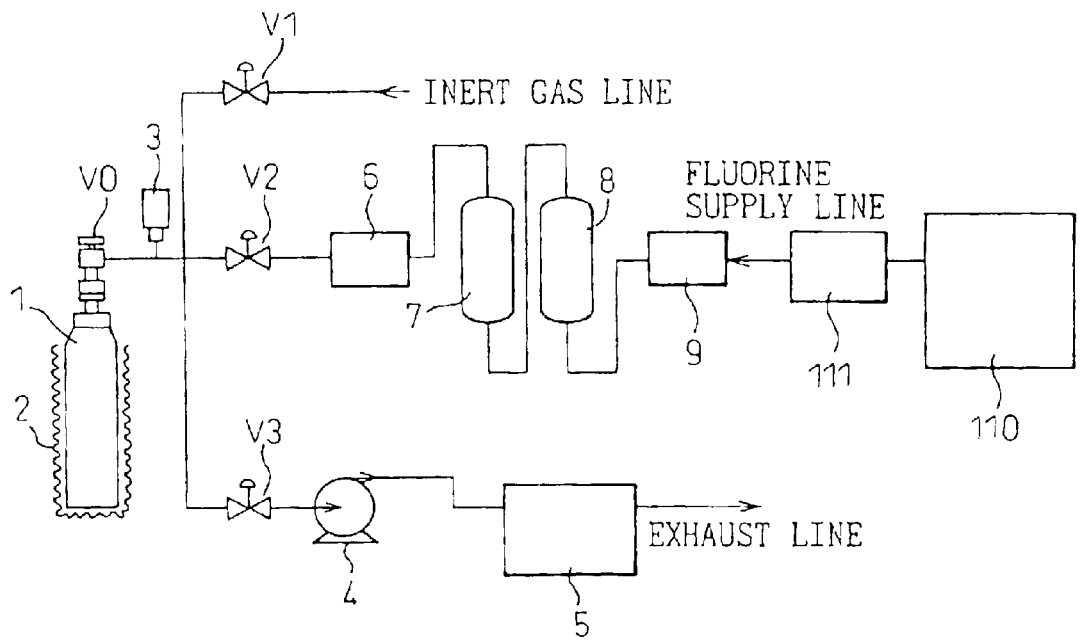
FIG. 1 is a view schematically showing an embodiment of the apparatus used for practicing the step (2) in the production process of the high-purity fluorine gas of the present invention.

In the drawings, 1 denote a fluorine generator, 2 a heater, 3 a pressure gauge, 4 a vacuum pump, 5 an exhaust gas treating tube, 6 and 9 mass flow controllers, 7 a fluorine tank, 8 an NaF column, 110 an electrolytic cell, 111 an HF condenser, 210 a fluorine gas cylinder, 310 a fluorine generator, 311 a heater, 410 a fluorine supply source, 412 a fluorine tank, V0 to V6 valves, 11 to 23 valves, 24 a high-purity He gas, 25 a standard gap, 26 a high-purity $F_2$ gas, 27 a pressure gauge, 28 a heater, 29 a container containing a fluorine gas-removing and separating agent, 30 a gas chromatograph analyzer 1, 31 a gas chromatograph analyzer 2, 32 a gas cell for FT-IR, 33 an FT-IR analyzer, 34 a fluorine gas harm-removing cylinder, and 35 a vacuum pump.

BEST MODE FOR CARRYING OUT THE INVENTION

Examples of the main impurity gases contained in a fluorine gas include gases such as HF, $O_2$, $N_2$, $CO_2$, $CF_4$ and $SiF_4$. Among these impurity gases, HF can be relatively easily removed by using NaF. $CF_4$ and $SiF_4$ are relatively low in the concentration and in many cases, these are not impurities causing a problem in the quality. $N_2$ is an inert gas and therefore, the concentration thereof is in the allowable range in most cases. Among the above-described impurity gases, the impurity components difficult to remove and required to be in a low concentration are $O_2$ gas and $CO_2$ gas.

For example, in irradiating a laser on a rock in a fluorine gas atmosphere to determine the oxygen content thereof, the oxygen gas concentration in the fluorine gas must be as low as possible.

Furthermore, in producing a fluoride lens for an exposure system for use in the production of a semiconductor by an excimer laser, if an oxygen gas is contained, the transmittance decreases and therefore, the fluorine gas used must have a low oxygen gas concentration.

Also, in the case of light emission of an excimer laser using a fluorine gas, the fluorine gas filled in or supplied to the laser chamber must be a fluorine gas reduced in the impurity gas content including the oxygen gas concentration.

The high-purity fluorine gas obtained by using the production process of the present invention may be a fluorine gas having a purity of 99.7% or more.

The term "occluding" a fluorine gas as used herein refers to a phenomenon such that the fluorine gas forms a complex compound with a metal and by reaction, reaches the form of a fluorine compound. When a fluoronickel compound occludes the fluorine gas, the chemical change expressed, for example, as a reaction formula of $K_3NiF_6$ is shown by the following formula:

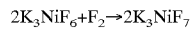

The term "releasing" a fluorine gas refers to a phenomenon of releasing the fluorine gas by the reverse reaction of the occlusion and when a fluoronickel compound releases the fluorine gas, the chemical change expressed, for example, as a reaction formula of $K_3NiF_7$ is shown by the following formula:

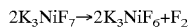

If an impurity gas contained in a fluorine gas is adsorbed to, for example, a fluoronickel compound, a state of physical adsorption occurs where the gas is drawn to the surface of a substance mainly by an intermolecular force with weak bonding strength. In this specification, the phenomena of such adsorption and desorption of impurity gas is expressed by the terms "adsorption" and "diffusion".

In the production process of a high-purity fluorine gas of the present invention, the step (3) of heating the fluoronickel compound filled in a container at 250 to 600° C. and reducing the pressure inside the container to 0.01 MPa (absolute pressure) or less is preferably conducted at a heating temperature of 280 to 500° C., more preferably from 300 to 450° C., under a pressure reduced to 0.001 MPa or less.

The production process of a high-purity fluorine gas of the present invention preferably comprises a step (4) of adjusting the temperature of the fluoronickel compound filled in the container to less than 250° C. and reducing the pressure inside the container to 0.01 MPa (absolute pressure) or less. In the step (4), the temperature is preferably adjusted to from 20° C. to less than 250° C., more preferably from 100° C. to less than 250° C., and the pressure is preferably reduced to 0.001 MPa or less.

The main purpose of the step (3) and the step (4) is to remove impurities previously present in the fluoronickel compound by allowing the impurities to diffuse from the fluoronickel compound. Depending on the heating temperature, the impurities can be removed by diffusion together with the release of the fluorine gas.

How long and how many times the step (3) and the step (4) are conducted can be appropriately selected according to the purpose. The step (3) is preferably conducted twice or more, more preferably three times or more. The time period of conducting the step (3) varies depending on the heating time but the step (3) is preferably conducted until a fluorine gas is not released from the fluoronickel compound. The step (4) is preferably conducted twice or more, more preferably three times or more.

The fluoronickel compound filled in the container is preferably at least one compound selected from the group consisting of $K_3NiF_5$, $K_3NiF_6$ and $K_3NiF_7$.

The step (1) is a step of heating a fluoronickel compound filled in a container to release a fluorine gas. The heating temperature is preferably 250 to 600° C. The size of the container where a fluoronickel compound is filled can be selected according to the amount of fluorine gas generated. The construction material of the container is preferably a corrosion-resistant material such as nickel, monel and stainless steel, more preferably the corrosion-resistant material of which surface is previously passivated with a fluorine gas. Also, a metal material of which surface is plated with nickel and then passivated with a fluorine gas may be used.

In the production process of a high-purity fluorine gas of the present invention, the fluoronickel compound repeatedly occludes and releases a fluorine gas, whereby impurities present in the fluoronickel compound itself can be removed and the fluorine gas generated can be elevated in the purity. However, the impurity HF may not be removed even by repeating occlusion and release and therefore, the fluorine gas used preferably has a hydrogen fluoride content of 500 vol ppm or less, more preferably 100 vol ppm or less. The fluorine gas used may be a crudely purified fluorine gas which is separately prepared. In the case where the released fluorine gas contains 500 vol ppm or more of HF, it is preferred that this fluorine gas is not re-used and re-occluded into a fluoronickel compound and the crudely purified fluorine is occluded after removing HF or the like.

This operation is performed not only for the purpose of reducing the HF concentration in the fluorine gas but also for facilitating the removal of impurity gases including $O_2$ gas and $CO_2$ gas. More specifically, it is considered that HF adsorbs to the fluoronickel compound and thereby the occlusion of a fluorine gas into the fluoronickel compound is prevented, or the HF-adsorbed fluoronickel compound readily takes in a substance such as $O_2$ gas or $CO_2$ gas and the removal thereof by diffusion becomes difficult.

In the step (2), the fluorine gas occluded into the fluoronickel compound is preferably an undiluted fluorine gas, the fluorine gas pressure is preferably 0.2 MPa or more, more preferably from 0.2 to 1.0 MPa, still more preferably from 0.3 to 0.8 MPa, and the temperature at the time of occluding a fluorine gas is preferably 100 to 400° C.

Each of FIGS. 1 to 4 is a schematic view showing an embodiment of the apparatus usable at the time of practicing the step (2) in the production process of a high-purity fluorine gas of the present invention. The fluoronickel compound is $K_3NiF_6$ and/or $K_3NiF_7$. Depending on the fluorine gas used as a raw material, any one of production apparatuses shown FIGS. 1 to 4 can be selected, however, the construction of the apparatus is not limited thereto.

In FIG. 1, a raw material fluorine gas is obtained in an electrolytic cell 110 for performing electrolysis of KF·HF or the like and used after HF contained as an impurity is mostly removed using a condenser 111. The fluorine generator 1 filled with a fluoronickel compound can be externally heated by a heater 2 under temperature control. The fluorine gas containing HF, in an amount of a few % or more, flows out from the electrolysis cell 110 for electrolyzing KF·HF or the like, is introduced into the condenser 111 to remove HF and then, while the flow rate is controlled by a mass flow controller 9, is introduced into an NaF column 8 filled with NaF to reduce the HF concentration in the fluorine gas to 500 vol ppm or less. The fluorine gas reduced in HF is once stored in a tank 7 or continuously passed through the tank 7 and then, while the flow rate is controlled by a mass flow controller 6, is supplied to the fluorine generator 1 through valves V2 and V0. Valve V1 is a valve of a purging inert gas line used at the time of fixing/removing the fluorine generator and the purged exhaust gas or the exhaust gas from the fluorine generator 1 is discharged through a valve V3 of the exhaust line, a vacuum pump 4 and an exhaust gas treating tube 5.

Figure 2:
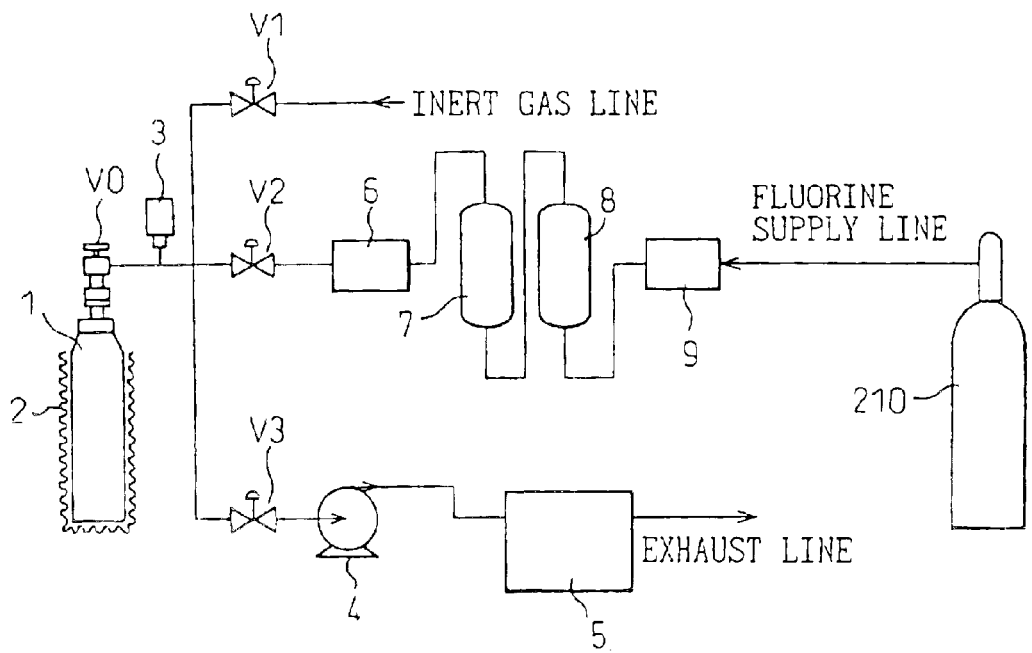
FIG. 2 is a view schematically showing another embodiment of the apparatus used for practicing the step (2) in the production process of the high-purity fluorine gas of the present invention.

In FIG. 2, the raw material fluorine gas is an undiluted cylinder fluorine gas 210 filled in a pressure-resistant container. The only difference from the process shown in FIG. 1 is the raw material fluorine. The fluorine filled in a cylinder does not contain 1 vol % or more of HF in many cases and the apparatus shown in FIG. 2 is constructed not to use an HF condenser.

Figure 3:
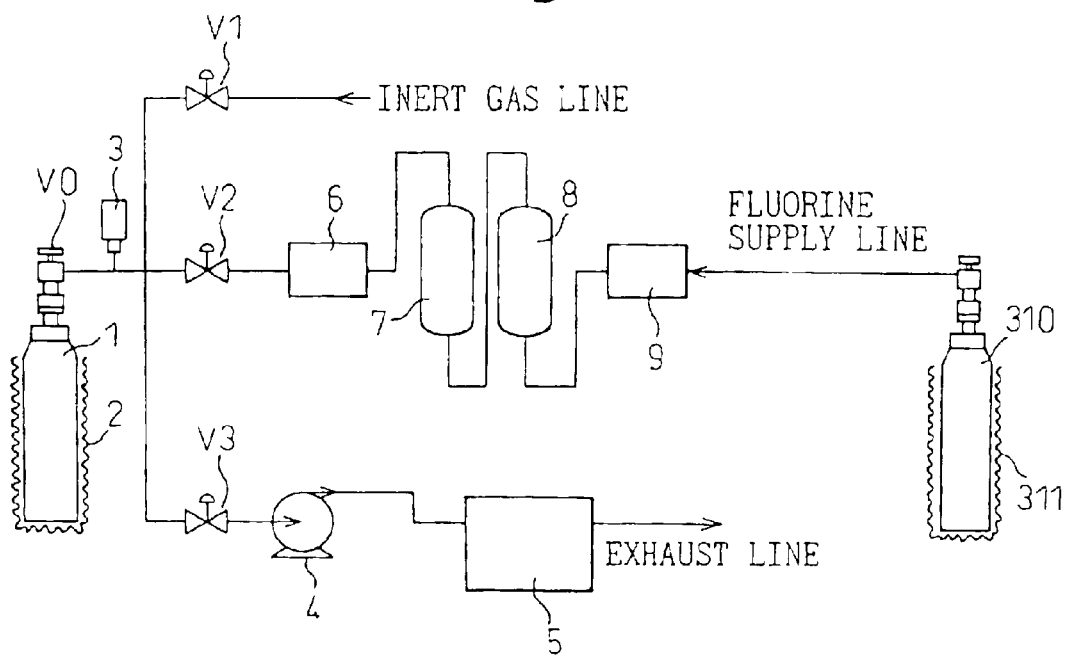
FIG. 3 is a view schematically showing a further embodiment of the apparatus used for practicing the step (2) in the production process of the high-purity fluorine gas of the present invention.

In FIG. 3, the raw material fluorine is a fluorine generator 310 filled with a fluoronickel compound in a state such that a high-purity fluorine gas is already occluded. The only difference from the process shown in FIG. 1 is the raw material fluorine. The fluorine generator 310 is attached with a heater 311 with temperature control for heating the fluorine generator 310. Similarly to the apparatus shown in FIG. 2, the apparatus shown in FIG. 3 is constructed not to use an HF condenser.

Figure 4:
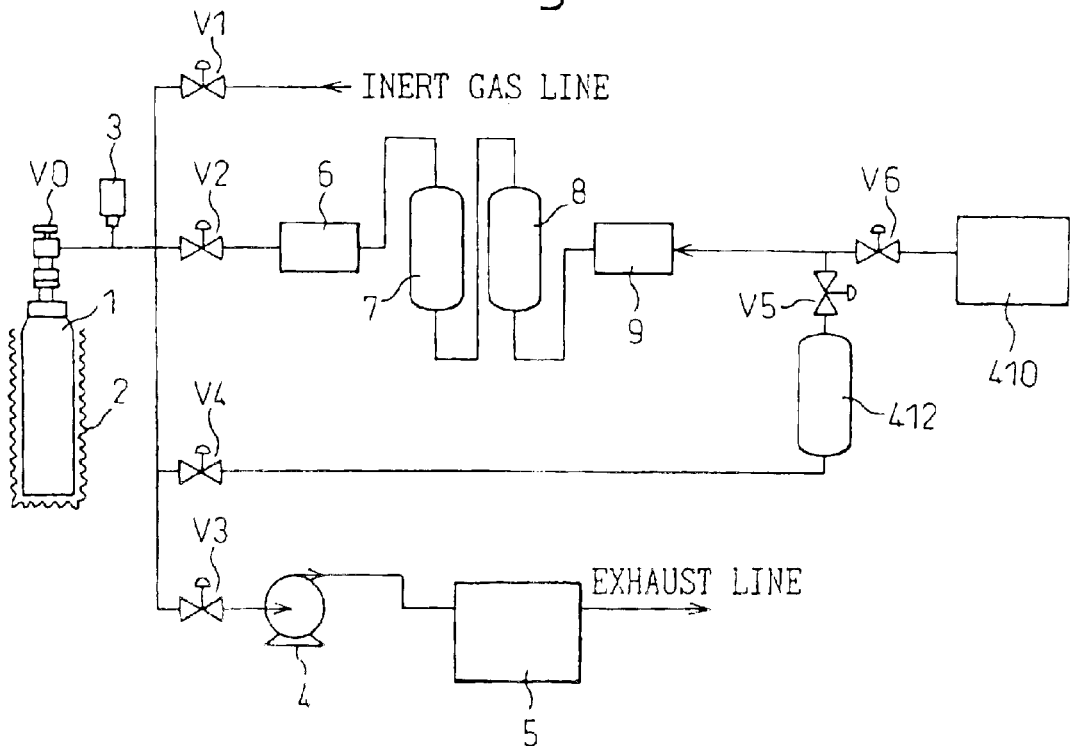
FIG. 4 is a view schematically showing a further embodiment of the apparatus used for practicing the step (2) in the production process of the high-purity fluorine gas of the present invention.

FIG. 4 shows a process using any one of three kinds of fluorine supply sources (110, 210 and 310) shown in FIGS. 1 to 3 and a tank 412 for storing the fluorine gas generated from the fluorine generator 1, where the fluorine gas used can be selected from fluorine gases obtained from different fluorine supply sources. Accordingly, the fluorine supply source 410 can be the unit comprising an electrolytic cell 110 for generating fluorine by the electrolysis of KF-HF or the like and a condenser 111 shown in FIG. 1, the cylinder fluorine 210 shown in FIG. 2 or the fluorine generator 310 shown in FIG. 3.

When the fluorine generator 1 is heated by the heater 2, the fluorine gas is once stored in a fluorine tank 412 through a valve V4. The fluorine gas obtained from the fluorine supply source 410 and the fluorine gas stored in the fluorine tank 412 can be selected and used by operating the valves V4, V5 and V6. More specifically, in the case of V4 CLOSE, V5 CLOSE and V6 OPEN, the fluorine can be supplied from the fluorine supply source 410; in the case of V4 CLOSE, V5 OPEN and V6 CLOSE, the fluorine gas can be supplied from the fluorine tank 412 through an NaF layer; and in the case of V4 OPEN, V5 CLOSE and V6 CLOSE, the fluorine gas can be supplied from the fluorine tank 412 without passing through the NaF layer.

In the foregoing pages, the fluoronickel compound is shown as $K_3NiF_6$ and/or $K_3NiF_7$. Here, $K_3NiF_7$ shows a state where fluorine is occluded, and $K_3NiF_6$ shows a state where fluorine is released. However, in each state, all of the compound is not strictly a simple $K_3NiF_6$ substance or a simple $K_3NiF_7$ substance but a mixture or transient state of $K_3NiF_6$ and $K_3NiF_7$ is present. For example, the $K_3NiF_7$ showing the state where fluorine is occluded contains from 5 to 30% of $K_3NiF_6$.

The production process of a high-purity fluorine gas of the present invention is described in detail below by referring to the case using $K_3NiF_7$ as a fluoronickel compound having occluded therein fluorine.

(1) The fluoronickel compound $K_3NiF_7$ is filled in a container and the filled container is heated to, for example, from 110 to 200° C. and depressurized to 0.01 MPa (absolute pressure) or less, thereby performing the vacuum drying. The water content in the co-presence of fluorine is converted into HF or the like and by performing this operation, impurities such as HF can be removed by diffusion. The next operation (2) is to perform the operation of (1) at a higher temperature and therefore, the operation (1) may be omitted.

(2) A container filled with the fluoronickel compound $K_3NiF_7$ is continuously depressurized by a vacuum pump and under reduced pressure of 0.01 MPa (absolute pressure) or less, externally heated to 250 to 600° C. by a heater to release a fluorine gas, and the state where a fluorine gas is not released at this temperature any more is confirmed by the pressure or the like. On releasing the fluorine gas, impurities including HF remaining without diffusing in the operation of (1) can be removed by diffusion. At this time, $K_3NiF_7$ is considered to mostly convert into $K_3NiF_6$ due to the release of fluorine gas.

(3) A fluorine gas is crudely purified so that the fluorine gas can be re-occluded into the $K_3NiF_6$ obtained in the operation of (2). This is performed mainly to remove HF. The crude purification may be performed, for example, by passing a raw material fluorine gas to a column filled with sodium fluoride (NaF) at a flow rate of 500 ml/min or less. This operation may be performed in series with the next operation of re-occluding a fluorine gas. The raw material fluorine gas used here may be the fluorine gas released in the operation of (2) and once stored in a tank or the like, or a fluorine gas released by heating another container filled with a fluoronickel compound $K_3NiF_7$. Of course, the undiluted fluorine gas filled in the pressure-resistant container or the fluorine gas obtained by the electrolysis of KF·HF or the like may be used after removing most of HF.

(4) A fluorine gas is again occluded into the fluoronickel compound $K_3NiF_6$. The fluorine gas used here is preferably the fluorine gas crudely purified in (3). As for the conditions in allowing a fluorine gas to be occluded into the fluoronickel compound, an undiluted fluorine gas is used, the fluorine gas pressure is set to 0.2 MPa or more as an absolute pressure, and heating is externally performed to 150 to 300° C. by a heater or the like.

(5) The fluoronickel compound having newly occluded therein a fluorine gas is heated, for example, to 300 to 450° C., whereby a high-purity fluorine gas is obtained.

By performing these operations (1) to (5), a high-purity fluorine gas having a purity of 99.7% or more can be obtained. In order to obtain higher purity fluorine gas, this may be attained by repeating the operations (1) to (5) until a fluorine gas having a desired purity can be obtained. However, the operation of (1) is performed for the purpose of removing by diffusion HF and the like initially present in the fluoronickel compound and therefore, may be omitted in the second time and later. Usually, in order to obtain a high-purity fluorine having a purity, for example, of 99.9 vol % or more, the occlusion and release of fluorine into and from the fluoronickel compound are preferably repeated twice or more. Also, in order to obtain a high-purity fluorine having a purity of 99.99 vol % or more, the occlusion and release of fluorine into and from the fluoronickel compound are preferably repeated three times or more.

Also, in order to obtain a high-purity fluorine gas, the following operation (6) may be performed, for example, after the operation of (4). The operation of (6) is to reduce the pressure by a vacuum pump at a temperature of less than 250° C. after the operation of (4) and thereby remove impurity gases such as $O_2$ gas and $CO_2$ gas. At this time, in the vicinity of 250° C., impurities such as $O_2$ gas and $CO_2$ gas can be readily removed but release of a fluorine gas also occurs. Accordingly, this operation is preferably performed at 100 to 200° C. where the loss of fluorine is not large and the effect of removing impurities such as $O_2$ and $CO_2$ is high.

The high-purity fluorine gas of the present invention is described below.

The high-purity fluorine gas of the present invention is a high-purity fluorine gas recovered, after a step (1) of heating a fluoronickel compound filled in a container to release a fluorine gas and a step (2) of allowing a fluorine gas to be occluded into a fluoronickel compound filled in a container are conducted, in the step (1), which is recovered in the step (1), after the step (2) in which a fluorine gas reduced in a hydrogen fluoride content to 500 vol ppm or less is occluded as well as a step (3) of heating the fluoronickel compound filled in a container at 250 to 600° C. and reducing a pressure inside the container to 0.01 MPa (absolute pressure) or less are conducted, respectively, at least once.

Also, the high-purity fluorine gas of the present invention is a high-purity fluorine gas recovered, after a step (1) of heating a fluoronickel compound filled in a container to release a fluorine gas and a step (2) of allowing a fluorine gas to be occluded into a fluoronickel compound filled in a container are conducted, in the step (1), which is recovered in the step (1), after the step (2) in which a fluorine gas reduced in a hydrogen fluoride content to 500 vol ppm or less is occluded as well as a step (3) of heating the fluoronickel compound filled in a container at 250 to 600° C. and reducing a pressure inside the container to 0.01 MPa (absolute pressure) or less and a step (4) of reducing a pressure inside the container filled with the fluoronickel compound to 0.01 MPa (absolute pressure) or less at a temperature of less than 250° C. are conducted, respectively, at least once.

The fluoronickel compound filled in a container is preferably at least one compound selected from the group consisting of $K_3NiF_5$, $K_3NiF_6$ and $K_3NiF_7$.

The purity of the fluorine gas may be 99.9 vol % or more and a high-purity fluorine gas having a purity of 99.99 vol % or more can also be obtained.

The oxygen gas content of the fluorine gas may be 10 vol ppm or less and the carbon dioxide gas content may be 10 vol ppm or less.

According to an experiment by the present inventors, when conventional cylinder fluorine gases were analyzed, the purity of fluorine gas was 99.69 vol %, the content of HF contained as an impurity was 1,500 vol ppm, the content of $O_2$ gas was 200 vol ppm, the content of $CO_2$ gas was 250 vol ppm, the content of $N_2$ gas was 500 vol ppm, the content of $CF_4$ was 400 vol ppm and the content of $SiF_4$ was 250 vol ppm. From this, it is understood that the fluorine gas of the present invention is a high-purity fluorine gas reduced in impurity gas contents.

The contents of oxygen gas, carbon dioxide gas and the like contained in the fluorine gas can be determined, for example, by allowing a fluorine gas to be occluded into $K_3NiF_6$ as a fluoronickel compound and analyzing the non-occluded oxygen gas, carbon dioxide gas and the like using a gas chromatograph. The purity of fluorine gas can be obtained by subtracting the contents of these impurities from 100%.

The high-purity fluorine gas of the present invention can be used, for example, as an excimer laser gas.

The high-purity fluoronickel compound which can produce the high-purity fluorine gas of the present invention is described below.

The high-purity fluoronickel compound of the present invention can repeatedly perform the occlusion and release of a fluorine gas and release a high-purity fluorine gas. The high-purity fluoronickel compound can be obtained by conducting a step (4) of reducing the pressure within a container filled with a fluoronickel compound to 0.01 MPa (absolute pressure) or less at a temperature of less than 250° C., a step (3) of heating the fluoronickel compound filled in the container to 250 to 600° C. and reducing the pressure within the container to 0.01 MPa (absolute pressure) or less, and a step of occluding a fluorine gas reduced in the hydrogen fluoride content to 500 vol ppm or less, respectively, at least once. The fluoronickel compound is preferably at least one compound selected from the group consisting of $K_3NiF_5$, $K_3NiF_6$ and $K_3NiF_7$.

Next, the method for analyzing trace impurities in a high-purity fluorine gas will be explained below.

As described above, in analyzing a fluorine gas, the fluorine gas reacts with an oxide on the inner surface of pipeline, container, valve and the like, or with $H_2O$ adsorbed to the metal surface to generate $O_2$ and HF which cause a problem of contamination. In order to solve this problem, the method for analyzing trace impurities in a high-purity fluorine gas of the present invention is characterized by performing a pretreatment of metal materials. In the present invention, a fluoronickel compound which is a fluorine gas-occluding substance is used as the fluorine gas-removing and separating agent and the fluoronickel compound is sometimes referred to as a fluorine gas-removing and separating agent.

In the analysis method of the present invention, a fluorine gas is contacted with, for example, a fluorine gas-removing and separating agent to fix the fluorine gas to the fluorine gas-removing and separating agent and the separated trace impurities are analyzed by gas chromatography using a separation column packed with porous polymer beads, molecular sieve 5A, or the like, according to the objective component.

The present invention is directed to a method for analyzing trace impurities in a fluorine gas which is useful as a gas for etching, cleaning, an excimer laser, annealing of metal fluoride, fluorination of a material and the like. Among these, use in the fields requiring a high-purity fluorine gas for etching, excimer laser and annealing of metal fluoride is intended, however, the analysis method of the present invention is not limited to the high-purity fluorine gas.

The method for analyzing trace impurities in a high-purity fluorine gas of the present invention includes (1) a method using gas chromatography and (2) a method using infrared spectrophotometry.

The analysis method (1) of the present invention comprises filling a fluoronickel compound in a container comprising a metal material or a metal material having a nickel film, the container having a fluorinated layer formed on a surface of the metal material or nickel film, conducting a step (5) of heating the fluoronickel compound to 250 to 600° C. and reducing the pressure inside the container to 0.01 MPa (absolute pressure) or less, and a step (6) of allowing a fluorine gas reduced in a hydrogen fluoride content to 500 vol ppm or less to be occluded into the fluoronickel compound which has passed through the step (5), respectively, at least once, and further conducting the step (5), then contacting a fluorine gas containing impurity gases with the fluoronickel compound at 200 to 350° C. to fix and remove the fluorine gas, and analyzing the impurities by gas chromatography.

The analysis method (2) of the present invention comprises introducing a fluorine gas containing impurity gases into a cell with a material of window being composed of a metal halide, and analyzing the impurities by infrared spectrometry, the method using an apparatus where a fluorinated layer is formed on a surface of a metal material or metal material having nickel film which comes into contact with the fluorine gas.

In the analysis method of the present invention, on the surface of a metal material or metal material having nickel film which comes into contact with a fluorine gas, a fluorinated layer is preferably formed using a fluorine gas. For example, even in the case of an inexpensive stainless steel, nickel plating is applied to the surface and the nickel plated surface is fluorinated. The nickel plating can be performed by the method described, for example, in Japanese Unexamined Patent Publication No. 11-92912 (JP-A-11-92912). Also, the fluorinated layer can be formed on the surface of a metal material or metal material having nickel film by the method described, for example, in JP-A-11-92912.

For forming the fluorinated layer on the surface of a metal material or nickel film, a method of heat-treating the metal material or nickel film at 200 to 300° C. in the presence of an inert gas and fluorinating the surface using a fluorine gas reduced in the hydrogen fluoride content to 500 vol ppm or less may be used. Also, for forming the fluorinated layer on the surface of a metal material or nickel film, a method of forcibly oxidizing the surface of the metal material or nickel film and then fluorinating the surface using a fluorine gas reduced in the hydrogen fluoride content to 500 vol ppm or less may be used.

In the method for analyzing trace impurities in a high-purity fluorine gas according to the present invention, the pipeline, sampling line and the like used, which come into contact with a fluorine gas, are previously subjected to a treatment of an oxide on the inner surface or $H_2O$ adsorbed to the surface and at the same time, to a passivation treatment of the inner surface, a fluorine gas is fixed to a fluoronickel compound, and trace impurities contained in the fluorine gas, such as $H_2$, $O_2$, $N_2$, $CH_4$, CO, $CO_2$, $CF_4$, $SF_6$, $NF_3$, He, Ne, Ar, Kr and Xe, are introduced into a gas component separation column and measured by a detector such as TCD (thermal conductivity detector), PID (photoionization detector), DID (discharge ionization detector) or PDD (pulsed discharge detector). The components such as HF, $SiF_4$ and gaseous metal fluoride, for which an appropriate separation column is not available and which cannot be analyzed by gas chromatography, are introduced together with the fluorine gas directly into a cell for infrared spectroscopy and measured by Fourier transform infrared spectroscopy (FT-IR). According to this method, components such as $CO_2$, $CF_4$ and $SF_6$ can also be analyzed at the same time in addition to HF and $SiF_4$.

The method for treating the inner surface of a metal material used in practicing the present invention is specifically described below.

The analysis of trace impurities in a highly reactive gas such as fluorine gas can be first attained when the construction materials of the container, valve, pipeline, equipment and the like used therefor are carefully examined. In the analysis method of the present invention, a fluorinated layer is formed on the surface of a metal material or nickel film which comes into contact with a fluorine gas, whereby the problem of contamination by HF or $O_2$, generated due to $H_2O$ and the like adsorbed to the inner surface of a material coming into contact with a fluorine gas at the time of analysis, can be solved.

Each part (valve, container for filling fluorine gas-removing and separating agent, pipeline, pressure gauge) which comes into contact with a fluorine gas is baked under heating at 200 to 300° C., in the case where the construction material is, for example, a stainless steel, after applying nickel plating and in the case of nickel or monel, directly, and then heat-treated with a fluorine gas, whereby a fluoride film can be formed on the surface. The fluorine gas concentration is suitably from 5 to 20%, preferably from 5 to 15%. If the fluorine gas concentration is less than 5%, the formation of fluoride film may take time, whereas if it exceeds 20%, the formed film may be fragile. The temperature at the time of forming the fluoride film is suitably from 200 to 400° C. If the temperature is less than 200° C., the film formation may take long time, whereas if it exceeds 400° C., the formed film may be cracked and decreased in the corrosion resistance because $H_2O$ or the like is adsorbed to the crack. By forming as such a fluoride film on the inner surface of each part which comes into contact with a fluorine gas, the gas released from the metal surface can be reduced to a level of causing no problem in the analysis of trace impurities in a high-purity fluorine gas.

The fluoronickel compound (fluorine gas-removing and separating agent) used in the analysis method (1) of the present invention is described below.

The present invention is characterized in that $K_3NiF_5$ (potassium pentafluoronickelate) or $K_3NiF_6$ (potassium hexafluoronickelate) is used as the fluoronickel compound (fluorine gas-removing and separating agent). These compounds are each a powder solid substance and a fluorine gas-removing and separating agent utilizing the principle of occluding and releasing a fluorine gas by the change in temperature as shown in the following chemical formulae:

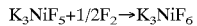
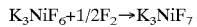

$$K_3NiF_5 + 1/2 F_2 \rightarrow K_3NiF_6$$

$$K_3NiF_6 + 1/2 F_2 \rightarrow K_3NiF_7$$

$$K_3NiF_7 \rightarrow K_3NiF_6 + 1/2 F_2$$

The fluoronickel compound (fluorine gas-removing and separating agent) for use in the present invention can be prepared, for example, by the following method.

In the preparation of a fluorine gas-removing and separating agent, $NiF_2$ and KF are used as starting materials and these are pulverized into an appropriate particle size and dried at 100 to 500° C. The obtained mixture is filled in a container with a valve, of which inner surface is previously subjected to a passivation treatment. The container filled with the fluorine gas-removing and separating agent is equipped with a heater and valves for the connection to the fluorine gas ($F_2$) and inert gas (He) containers and to a vacuum pump. An operation of heating the obtained $K_3NiF_5$ in vacuum under conditions of a temperature of 200 to 350° C. and a pressure reduction degree of 10 to 100 Pa, and an accumulated pressure purging operation using an inert gas are repeated several times to exhaust $H_2O$ and the like adsorbed to the material filled and the inner surface of container.

$K_3NiF_6$ can be obtained by allowing a fluorine gas to be occluded into the $K_3NiF_5$ obtained above. In order to obtain high-purity $K_3NiF_6$, this may be attained by repeating the occlusion and release of a fluorine gas several times to remove ultratrace impurities such as $H_2O$ and HF.

The concentration of a HF contained in a fluorine gas to be occluded into the fluoronickel compound is preferably reduced to 500 vol ppm or less. The HF concentration is preferably 100 vol ppm or less, more preferably 10 vol ppm or less. The HF concentration can be reduced by contacting the fluorine gas with sodium fluoride (NaF).

The fluoronickel compound for occluding a fluorine gas is preferably $K_3NiF_6$ which occludes a fluorine gas to produce $K_3NiF_7$ and can be easily regenerated by releasing the fluorine gas under heating. The heating temperature for regeneration is preferably 350° C. or more from the standpoint of removing not only the fluorine gas but also the HF adsorbed.

In the analysis method (1) of the present invention, high-purity $K_3NiF_6$ from which ultratrace impurities such as $H_2O$ and HF are removed is preferably used as the fluorine gas-removing and separating agent and this compound may contain $K_3NiF_7$.

The method for analyzing trace impurities in a high-purity fluorine gas using the analysis method (1) of the present invention is described below, where trace impurities contained in a fluorine gas, such as $N_2$, $O_2$, $CO_2$, fluorocarbon (e.g., $CF_4$) and $SF_6$, are separated from the fluorine gas and analyzed by gas chromatography.

$K_3NiF_6$ prepared as a fluorine gas-removing and separating agent is filled in a container in an amount sufficiently large to remove a fluorine gas, and a constant amount of fluorine gas containing impurities is enclosed in the container by the pressure indication, heated to 200 to 350° C. and gradually cooled to room temperature to allow the fluorine gas to be occluded into and fixed to the fluorine gas-removing and separating agent, whereby impurities contained in the fluorine gas are separated.

The impurities separated from the fluorine gas are diluted with a constant amount of inert gas and can be introduced into a gas chromatography as a gas not containing a fluorine gas, where the impurity content can be measured to 1 ppm or less.

The analysis method (2) of the present invention is described below and uses an apparatus where a metal material coming into contact with a fluorine gas is subjected to an inner surface treatment, and in which trace impurities contained in a fluorine gas, such as HF and $SiF_4$, are analyzed by an FT-IR.

In the analysis method (2) of the present invention, the inner surface of a metal material for pipeline or sampling line which comes into contact with a fluorine gas is fluorinated, whereby, similarly to the method (1) above, the adsorption of $H_2O$ to the inner surface can be inhibited as much as possible and the amount of (1) HF produced upon reaction of $F_2$ and $H_2O$ or (2) HF produced by the hydrolysis of $SiF_4$ which is one of impurities can be reduced and, as a result, trace impurities HF and $SiF_4$ contained in a fluorine gas can be measured to 1 ppm or less.

The present invention is further illustrated below by referring to Examples, however, the present invention is not limited to these Examples.

EXAMPLE 1

The apparatus shown in FIG. 4 was used and, as a fluorine supply source 410, an undiluted cylinder fluorine filled in a pressure-resistant container was used.

A monel 400-made fluorine generator 1 filled with a fluoronickel compound $K_3NiF_7$ was vacuum dried by an external heater 2 at a temperature of 150° C. under a pressure of 0.001 MPa (absolute pressure). The fluorine generator 1 was continuously depressurized by a vacuum pump 4 and under reduced pressure of 0.001 MPa (absolute pressure) and heated at 400° C. for 10 hours to release a fluorine gas. Then, from the fluorine cylinder 410, a fluorine gas was passed to a column 8 filled with sodium fluoride (NaF) at a flow rate of 100 ml/min and a crudely purified fluorine, after the removal of HF, was supplied directly to the fluorine generator 1 through a tank 7. As for the conditions at this time, the fluorine pressure was set to 0.4 MPa (absolute pressure) and the heating was externally performed to 250° C. Thereafter, the heating temperature was lowered to 200° C. and the pressure was reduced to 0.001 MPa (absolute pressure) by a vacuum pump 4. Then, the exhaustion by a vacuum pump was stopped and the heating temperature was elevated to 350° C. to obtain a fluorine gas. This fluorine gas was designated as Fluorine Gas (Example 1) and the analysis values thereof are shown in Table 1.

EXAMPLE 2

The fluorine generator 1 used in Example 1 was kept at a temperature of 350° C. and the generated fluorine was split into a previously vacuumized fluorine tank 412. Then, by closing the valve 4 and opening the valve 3, the fluorine occluded into the fluoronickel compound in the fluorine generator 1 was exhausted by a vacuum pump while heating at 350° C. to render the fluoronickel compound to be in a $K_3NiF_6$ state. The fluorine generator 1 was further continuously depressurized by a vacuum pump and under reduced pressure of 0.001 MPa (absolute pressure), heated at 400° C. for 10 hours. Subsequently, a fluorine gas was passed from the fluorine tank 412 to a column 8 filled with sodium fluoride (NaF) at a flow rate of 100 ml/min and the crudely purified fluorine, after the removal of HF, was supplied at 250° C. to the fluorine generator 1 through a tank 7.

The supply of fluorine gas was stopped, the temperature of heating the fluorine generator 1 was set to 200° C. and, while depressurizing by a vacuum pump, removal of impurity gases including $O_2$ and $CO_2$ was conducted. Thereafter, the exhaustion by a vacuum pump was stopped and the heating temperature was elevated to 350° C. to obtain a fluorine gas. This fluorine gas was designated as Fluorine Gas (Example 2) and the analysis values thereof are shown in Table 1.

EXAMPLE 3

In order to further reduce the impurity gases, subsequently to Example 2, the fluorine generator 1 was heated at 250° C. for 1 hour under reduced pressure of 0.001 MPa (absolute pressure). Thereafter, the exhaustion by a vacuum pump was stopped and the heating temperature was elevated to 350° C. to obtain a fluorine gas. This fluorine gas was designated as Fluorine Gas (Example 3) and the analysis values thereof are shown in Table 1.

TABLE 1

| | Purity | Concentration of Impurities [vol ppm] | | | | | |
|---|---|---|---|---|---|---|---|
| | [vol %] | HF | $O_2$ | $CO_2$ | $N_2$ | $CF_4$ | $SiF_4$ |
| Example 1 | 99.81 | 550 | 1100 | 100 | 100 | 10 | 10 |
| Example 2 | 99.95 | 100 | 300 | 20 | 20 | 5 | 5 |
| Example 3 | >99.99 | 20 | <10 | <10 | <10 | <1 | <1 |

EXAMPLE 4

Figure 5:
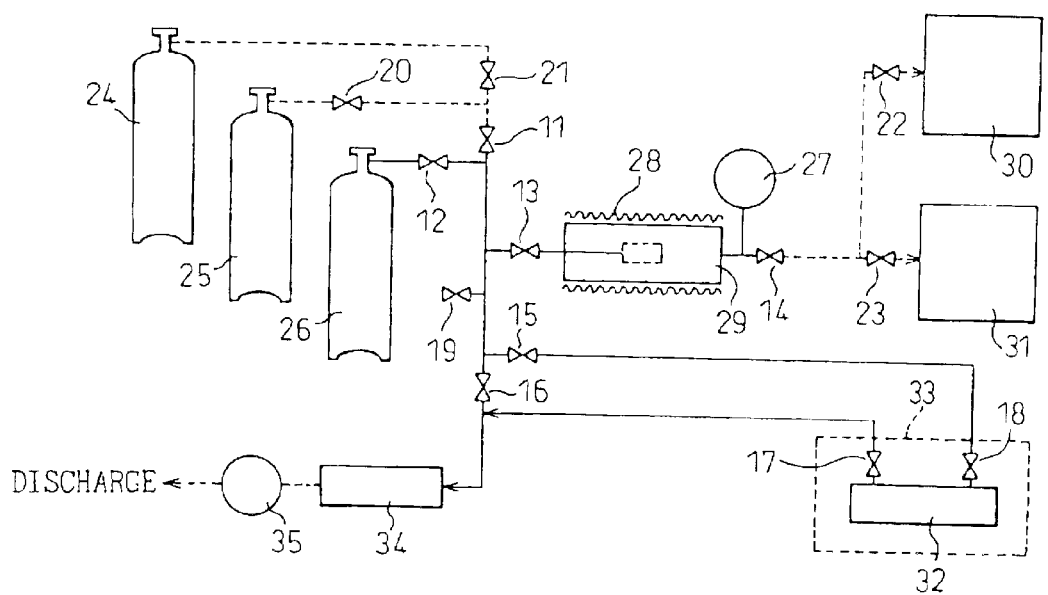
FIG. 5 is a view schematically showing an embodiment of the apparatus for use in the analysis method of high-purity fluorine gas of the present invention.

In an apparatus, shown in FIG. 5, for use in the analysis method of the present invention, each metal part of pipelines, valves 11 to 19, a pressure gauge 27, a container 29 (content volume: 500 ml), a cell 32 for FT-IR and a harm-removing cylinder 34 (content volume: 3 liters), which comes into contact with a fluorine gas, was subjected to nickel plating (film thickness: 5 to 10 Å). These equipments and materials were placed in an electric furnace capable of pressure reduction, baked at a temperature of 350° C. under reduced pressure and cooled. The pressure inside the electric furnace was again reduced and 10% $F_2$ diluted with $N_2$ gas was filled to an atmospheric pressure. Thereafter, the temperature was elevated to 350° C. at a temperature rising rate of 100° C./hour and the inside of the electric furnace was kept at 350° C. for 12 hours to allow the fluorination to proceed.

In this surface-treated container 29, 500 g of dried $K_3NiF_5$ powder (may be $K_3NiF_6$ or $K_3NiF_7$ separately prepared) was filled and the apparatus shown in FIG. 5 was composed. Valves 14, 16, 17, 19, 22 and 23 and main valves of containers 25 and 26 were closed, He 24 was filled to 0.1 MPa through a valve 21 and the line was confirmed to have no leakage.

Then, the line and valves were heated up to 150° C. by a tape heater and $H_2O$ slightly adsorbed at the time of composing the apparatus was purged with high-purity He 24 under heating in vacuum using the main valve of the He container, the valve 21 and a vacuum pump 35. After confirming the completion of purging with high purity He 24 under heating in vacuum by connecting a dew point analyzer to the valve 19 and making certain that the dew point of He was −80° C. or less, the next step was started.

By closing valves 11, 12, 14, 16, 17, 19, 20 and 21 and opening the $F_2$ main valve, $F_2$ was filled to a pressure of 0.1 MPa using a pressure gauge 27 and the valve 12 and left standing at a temperature of 150° C. for 2 hours, thereby performing a passivation treatment of the continuous line shown in FIG. 5. After confirming the completion of treatment by making certain that HF was 1 ppm or less by FT-IR, the next step was started.

Valves 11, 12, 14, 15, 16, 17 and 19 were closed, the entire system was cooled, the pressure was reduced using the valve 16 and the vacuum pump 35, the valve 16 was closed, the $F_2$ main valve was opened, $F_2$ was filled into the container 29 to 0.5 MPa using the pressure gauge 27 and the valve 12, the main valve and the valves 12, 13 and 14 were closed, the inner temperature of the container 29 was elevated to 500° C. by a heater 28 at a temperature rising rate of 100° C./hour, and the container was immediately cooled to 250° C. After cooling to 250° C., the valve 13 and the main valve were opened, $F_2$ was again filled in the container 29 to 0.5 MPa using the pressure gauge 27 and the valve 12, the valves 13 and 14 were closed, the inner temperature of the container 29 was elevated 500° C. by the heater 28 at a temperature rising rate of 100° C./hour, and the container was immediately cooled to 250° C. This operation was repeated until the reduction of pressure did not occur. Then, the next step was started.

In the state at a temperature of 250° C., the closing of valves 11, 12, 14, 15, 17 and 19 was again confirmed and $F_2$ inside the system was exhausted using the valve 16 and a vacuum pump 36 while rendering the gas harmless through a soda lime-filled harm-removing cylinder 34. After confirming the completion of exhaustion by the pressure gauge 27, the valve 16 was closed, the valve 13 and the main valve were opened again, $F_2$ was filled in the container 29 to 0.5 MPa using the pressure gauge 27 and the valve 12, the system was kept for 1 to 2 hours, and then $F_2$ inside the system was exhausted using the valve 16 and the vacuum pump 35 while rendering the gas harmless through a soda lime-filled harm-removing cylinder 34. This operation was repeated until HF was confirmed to be 1 ppm or less by FT-IR. After cooling to room temperature, pressure was applied by high-purity He 24, as a result, a fluorine gas-removing and separating agent ($K_3NiF_6$) was obtained in the container 29.

EXAMPLE 5

The line subjected to a fluorination treatment in Example 4 was used. After confirming that all valves were closed, the valves 15, 17 and 18 were opened and high-purity He 24 was introduced into an FT-IR cell 32 (see-through window: $CaF_2$, length: 150 mm). Furthermore, after confirming that the background was 1 ppm or less from the absorption of $CO_2$ at 2,350 cm$^{-1}$, a standard gas 25 (He base) and, through the valve 20, standard gases of HF (10 ppm, 4,040 cm$^{-1}$), $SiF_4$ (10 ppm, 1,016 cm$^{-1}$) and $CF_4$ (10 ppm, 1,280 cm$^{-1}$) were introduced into the FT-IR cell 32 and a calibration curve was prepared.

The $F_2$ main valve was opened, $F_2$ was introduced into the FT-IR cell 32 using the valve 12, and HF, $SiF_4$ and $CF_4$ in the high-purity $F_2$ were quantitatively analyzed from the calibration curve prepared above.

EXAMPLE 6

The line subjected to a fluorination treatment in Example 4 and the fluorine gas-removing and separating agent ($K_3NiF_6$) in the container 29 were used. After confirming that all valves were closed, the valves 12 and 13 were opened, the pressure inside the system was reduced by the vacuum pump 35 and the valve 16, the valve 16 was closed, the high-purity He main valve and the valve 21 were opened, and He gas was filled to 0.1 MPa using the valve 11 and the pressure gauge 27. System purging operation of this operation and evacuating the He gas were repeated three times or more. Furthermore, high-purity He 24 was filled to 0.1 MPa using the valve 11 and the pressure gauge 27, He in the system was introduced into a GC analyzer 30 using the valves 14 and 22 and after the background $O_2$ and $N_2$ each was confirmed to be 0.1 ppm or less by a gas separation column (molecular sieve 5A) and a PDD (pulsed discharge detector, manufactured by U.S. Valco) gas detector, the next step was started.

After once confirming that all valves were closed, the valves 12 and 13 were opened, the pressure inside the system was reduced using the valve 6 and the vacuum pump 35, the valves 12 and 16 were closed, $F_2$ in the high-purity container 26 and the generation unit was filled to 0.1 MPa using the valve 12 and the pressure gauge 27, the valves 12 and 13 were closed, and the inner temperature of the container 29 filled with the fluorine gas-removing and the separating agent ($K_3NiF_6$) temperature was elevated to 300° C., kept at 300° C. for several minutes and then cooled to room temperature. On the other hand, $F_2$ remaining inside the system surrounded by the valves 11, 12, 13, 15, 16 and 19 was rendered harmless and exhausted through the $F_2$ harm-removing cylinder 34 by opening the valve 16 while purging with high-purity He 24 using the valve 11. Thereafter, the valves 11 and 21 were opened and high-purity He 24 was filled through the valve 13 to 0.1 MPa using the pressure gauge 27 similarly to $F_2$. In the GC analyzer 30, $H_2$, $O_2$, $N_2$, $CH_4$ and CO were analyzed and in the GC analyzer 31 (gas separation column (POLAPACK Q, produced by Waters), PDD gas detector), $CO_2$, $CF_4$ and $SF_6$ were quantitatively determined.

Industrial Applicability

As described in the foregoing pages, according to the present invention, the concentrations of $O_2$ gas, $CO_2$ gas and the like contained as impurities in a fluorine gas can be reduced and a high-purity fluorine gas can be obtained. In particular, a fluorine gas having a purity of 99.99 vol % or more, which has been difficult to obtain by conventional techniques, can be obtained.

Further, according to the present invention, the contamination from an equipment or materials or the fluorine gas-removing and separating agent coming into contact with a fluorine gas can be inhibited and trace impurities contained in a high-purity fluorine gas can be analyzed.

What is claimed is:

1. A process for producing a high-purity fluorine gas, comprising:

(1) heating a fluoronickel compound in a container at a temperature from 280 to 500° C. under a reduced pressure of 0.01 MPa or less (absolute pressure), thereby releasing a fluorine gas and impurities, (2) occluding a fluorine gas into said fluoronickel compound, (3) heating the fluoronickel compound in the container at a temperature from 280 to 500° C. under a reduced pressure of 0.01 MPa or less (absolute pressure), thereby obtaining a high-purity fluorine gas, wherein each step is performed at least once.

2. The process according to claim 1, further comprising adjusting the temperature of the fluoronickel compound to less than 250° C. and reducing the pressure inside the container to 0.01 MPa or less (absolute pressure) after occluding the fluorine gas, thereby removing impurity gases.

3. A process according to claim 1 or 2, wherein the fluoronickel compound filled in a container is at least one compound selected from the group consisting of $K_3NiF_5$, $K_3NiF_6$ and $K_3NiF_7$.

4. A process according to claims 1 or 2, wherein the hydrogen fluoride content of the fluorine gas occluded into the fluoronickel compound is 500 vol ppm or less.

5. A method for analyzing trace impurities in a high-purity fluorine gas, comprising:

filling a container comprising a metal material or a metal material having a nickel film with a fluoronickel compound, said container having a fluorinated layer formed on a surface of the metal material or nickel film, heating said fluoronickel compound to 280 to 500° C. and reducing a pressure inside the container to 0.01 MPa or less (absolute pressure), occluding a fluorine gas having a hydrogen fluoride content to 500 vol ppm or less into said fluoronickel compound, heating said fluoronickel compound to 280 to 500° C. and reducing the pressure inside the container to 0.01 MPa or less (absolute pressure), then contacting the fluorine gas containing impurity gases with said fluoronickel compound at a temperature of from 200 to 350° C. to fix and remove the fluorine gas, and analyzing the impurities by gas chromatography.

6. The method according to claim 5, wherein the fluorinated layer on the surface of the metal material or nickel film is formed by heat-treating the surface of the metal material or nickel coating at 200 to 300° C. in the presence of an inert gas and fluorinating the surface using a fluorine gas reduced in the hydrogen fluoride content to 500 vol ppm or less.

7. The method according to claim 5, wherein the fluorinated layer on the surface of the metal material or nickel film is formed by forcibly oxidizing the surface of the metal material or nickel film and fluorinating the surface using a fluorine gas reduced in the hydrogen fluoride content to 500 vol ppm or less.

8. The method according to claim 5, wherein the fluoronickel compound filled in the container is at least one compound selected from the group consisting of $K_3NiF_5$, $K_3NiF_6$ and $K_3NIF_7$.

9. The method according to claim 5, wherein the trace impurities are at least one gas selected from the group consisting of $H_2$, $O_2$, $N_2$, $CH_4$, CO, $CO_2$, $CF_4$, $SF_6$, $NF_3$, He, Ne, Ar, Kr and Xe.

* * * * *